United States Patent
Buijsse (12)

(10) Patent No.: US 9,017,727 B2
(45) Date of Patent: Apr. 28, 2015

(54) AMINO ACID COMPOSITION WITH IMPROVED DISPERSIBILITY

(75) Inventor: Carla Angèle Paula Buijsse, Wageningen (NL)

(73) Assignee: N.V. Nutricia (NL)

( * ) Notice: Subject to any disclaimer, the term of this patent is extended or adjusted under 35 U.S.C. 154(b) by 55 days.

(21) Appl. No.: 13/500,662

(22) PCT Filed: Oct. 11, 2010

(86) PCT No.: PCT/NL2010/050672
§ 371 (c)(1),
(2), (4) Date: Jun. 20, 2012

(87) PCT Pub. No.: WO2011/043670
PCT Pub. Date: Apr. 14, 2011

(65) Prior Publication Data
US 2012/0251633 A1 Oct. 4, 2012

(30) Foreign Application Priority Data
Oct. 9, 2009 (WO) ............... PCT/NL2009/050613

(51) Int. Cl.
| | | |
|---|---|---|
| A61K 9/14 | (2006.01) | |
| A23L 1/305 | (2006.01) | |
| A23L 1/00 | (2006.01) | |
| A61K 9/16 | (2006.01) | |
| A61K 31/195 | (2006.01) | |
| A61K 31/198 | (2006.01) | |
| A61K 31/401 | (2006.01) | |
| A61K 31/714 | (2006.01) | |
| A61K 33/04 | (2006.01) | |
| A61K 45/06 | (2006.01) | |
| A61K 47/18 | (2006.01) | |
| A61K 47/42 | (2006.01) | |

(52) U.S. Cl.
CPC ............... *A23L 1/305* (2013.01); *A23L 1/0017* (2013.01); *A61K 9/1617* (2013.01); *A61K 9/1682* (2013.01); *A61K 31/195* (2013.01); *A61K 31/198* (2013.01); *A61K 31/401* (2013.01); *A61K 31/714* (2013.01); *A61K 33/04* (2013.01); *A61K 45/06* (2013.01); *A61K 47/183* (2013.01); *A61K 47/42* (2013.01)

(58) Field of Classification Search
None
See application file for complete search history.

(56) References Cited

U.S. PATENT DOCUMENTS

| 3,697,287 A | * | 10/1972 | Winitz ............................ 426/73 |
| 6,337,084 B1 | | 1/2002 | Stevens et al. |
| 2005/0106310 A1 | | 5/2005 | Green et al. |
| 2006/0115555 A1 | | 6/2006 | Foulger et al. |

FOREIGN PATENT DOCUMENTS

| EP | 0743016 A1 | 11/1996 |
| EP | 1479300 A1 | 11/2004 |
| EP | 1738755 A1 | 1/2007 |
| WO | 0151026 A2 | 7/2001 |
| WO | 2004034986 A2 | 4/2004 |
| WO | 2007014311 A2 | 2/2007 |

OTHER PUBLICATIONS

International Search Report relating to corresponding PCT/NL2010/050672, issued Nov. 26, 2010.
International Preliminary Report on Patentability relating to corresponding PCT/NL2010/050672, issued Feb. 2, 2012.

* cited by examiner

*Primary Examiner* — Snigdha Maewall
(74) *Attorney, Agent, or Firm* — Banner & Witcoff, Ltd.

(57) ABSTRACT

The invention relates to agglomerated amino acid particles comprising between 1 and 95 wt % of at least one component selected from the group of amino acids and peptides, including esters thereof and salts thereof, having a solubility in water at 20 degrees Celsius of less than 5 g/100 ml, wherein said at least one component is agglomerated with at least one water soluble amino acid, which may be a free amino acid, an ester thereof or a salt thereof, having a solubility in water at 20 degrees Celsius of at least 5 g/100 ml.

11 Claims, No Drawings

AMINO ACID COMPOSITION WITH IMPROVED DISPERSIBILITY

RELATED APPLICATION DATA

This application is a National Stage Application under 35 U.S.C. 371 of co-pending PCT application PCT/NL2010/050672 designating the United States and filed Oct. 11, 2010; which claims the benefit of PCT application PCT/NL2009/050613 and filed Oct. 9, 2009 each of which are hereby incorporated by reference in their entireties.

The present invention relates to a method for preparing a composition comprising amino acids and to a composition comprising amino acids.

Many nutritional products are made for specific medical indications that comprise significant amounts of free amino acids. Most of these products are in powder form since amino acids in liquid form suffer from chemical instability problems. Further, some amino acids are relatively insoluble in water compared to other amino acids.

Mixtures or amino acids having a low solubility may suffer from a bad dispersibility in aqueous liquid media, resulting in lump formation. This problem has been recognized in the past. E.g. WO 2008/130236 discloses a method using phospholipids for coating hydrophobic amino acids, in order to improve dispersibility of particles of hydrophobic amino acids.

WO2005/096835 discloses the use of lecithin for improving the dispersibility of food compositions.

It has also been proposed to improve the dispersibility of a powder comprising amino acids by coating the powder particles with a sugar. However, the use of sugars as a coating agent may cause considerable maillardation of the amino acids, during the coating process, and/or during storage. This has a negative effect on the color (browning of the product), on the taste and possibly on the quality/availability of the amino acids.

Another disadvantage of the solutions proposed in the prior art is that an additive has to be included in the composition that is not a required nutrient or even unwanted, in particular in infant formulae.

Additionally, the particle size distribution of commercially available powders of amino acid mixtures has a very broad range. This has the disadvantage that particles are susceptible to becoming unequally distributed when packaged as a loose powder, due to demixing. If costumers than scoop the powder, the powder on the top will not have the same amino acid content as the powder on the bottom of the container. Obviously this is an unfavorable situation that may lead to wrongly dosing the composition.

Moreover, the individual particles of known amino acid mixtures (in powder form) contain various particles with diverse properties may show considerable differences in solubility and/or wettability.

Finally, commercially available non-agglomerated powders of amino acid mixtures suffer from the problem of dust formation since some particles of amino acids are very small and/or have a low density, compared to other particles in the powder. There is thus a clear need to improve the properties of amino acid mixtures in powder form.

It is an object of the invention to address one or more of the disadvantages of the above described prior art technology.

The inventors surprisingly found that the wettability of particles of specific amino acids (in a powder), that are badly dispersible in water, is improved by providing agglomerates of these amino acid particles with water soluble amino acids.

Accordingly, the present invention relates to agglomerated amino acid particles comprising between 1 and 95 wt % of at least one component selected from the group of amino acids and peptides, including esters thereof and salts thereof, having a solubility in water at 20 degrees Celsius of less than 5 g/100 ml, wherein said at least one component is agglomerated with at least one water soluble amino acid, which may be a free amino acid, an ester thereof or a salt thereof, having a solubility in water at 20 degrees Celsius of at least 5 g/100 ml, in particular of at least 10 g/100 ml, more in particular of at least 15 g/100 ml.

The agglomerated amino acid particles may in particular be a in the form of a powder, or dispersed in a liquid, in particular an aqueous liquid.

In accordance with the invention, it is possible to provide agglomerated particles comprising one or more amino acids and/or one or more peptides having a solubility in water at 20 degrees Celsius of less than 5 g/100 ml that is well-dispersible in water without needing additives other than said water soluble amino acid.

Accordingly, if desired, the agglomerated particles of the invention may be free of reducing sugars and/or be free of lecithine and/or be free of phospholipids, and/or be free of any other agglomeration agents (agglomerants), other than water-soluble amino acids.

Further, it has been found that agglomerated particles according to the invention can be dispersed well in an aqueous liquid without any substantial formation of large lumps.

In the context of this document, the term wettability is equivalent to time to wet and disperse the particles of a powder in a solution (water). A good wettability of an amino acid containing powder is beneficial since it is a requisite for a good dispersibility in the liquid and reduces the time needed to prepare a liquid composition from a powder. A related benefit is an improved appreciation by the consumer (which is favorable for the nutritional status/well being of the consumer).

The wettability is defined as the time in seconds required for all the particles of a dry powder to become wetted (to sink below the water surface or assume a 'typical' wet appearance) when placed on the surface of water. The wettability may be measured using the IDF standard 87 (IDF 1979) developed by the International Dairy Federation (see "*IDF* 087.1979—*Instant dried milk—Determination of the dispersibility & wettability*"). This method is applicable for food and non-food powders. The IDF standard 87 is a rapid routine method to determine wettability, as is described in "*Food powders: physical properties, processing, and functionality*", by Gustavo V. Barbosa-Cànovas et al., 2005, page 88. In the examples below a method is given that may be used routinely to determine the wettability (wetting time) in water of instant dried powder products. This method is known as the GEA Niro Method No. A 5 b, and is derived from IDF standard 87 (1979) and uses equipment from Niro for the measurements. This method gives identical, or at least similar, wettability values as the IDF standard 87. Both methods can be suitably used to determine the wettability.

Preferably the time to wet (wettability) of amino acid compositions according to the invention is less than 60 seconds, more preferably in the range of 1 to 30 seconds.

When referring herein to amino acids and peptides respectively, this term is meant to include amino acids respectively peptides in their zwitterionic form (in which an amino group is in the protonated and a carboxylate group is in the deprotonated form), the amino acid respectively peptide in which an amino group is protonated and a carboxylic group is in its neutral form, and the amino acid respectively peptide in which an amino group is in its neutral form and a carboxylate group is in the deprotonated form, as well as salts thereof and esters thereof. The term 'amino acid' as used herein also encompasses non-peptidic oligomers, in particular dimers of amino acid monomers, such as cystine.

Solubility is the property of a chemical substance called solute to dissolve in a liquid solvent to form a homogeneous solution.

Herein after, the term 'lowly soluble amino acid(s)' respectively 'lowly soluble peptide(s)' is used for amino acids respectively peptides having a solubility in water at 20 degrees Celsius of less than 5 g/100 ml.

The lowly soluble peptides are in general selected from the group of oligopeptides having 2-10 amino acid units, in particular from the group of dipeptides, tripeptides, tetrapeptides and pentapeptides.

The lowly soluble amino acid(s) may in particular be selected from the group of group consisting of glutamine, leucine, isoleucine, valine, threonine, tyrosine, phenylalanine, asparagine, histidine, methionine, cystine, tryptophane, including esters and salts thereof. The lowly soluble peptide(s) may in particular comprise one or more of amino acid units selected from the group consisting of glutamine, leucine, isoleucine, valine, threonine, tyrosine, phenylalanine, asparagine, histidine, methionine, cystine, tryptophane.

Hereinafter, the term 'water soluble amino acid(s)' will be used for amino acids with a solubility in water at 20 degrees Celsius of at least 5 g/100 ml, in particular of at least 10 g/100 ml, more in particular of at least 15 g/100 ml.

Preferably. one or more water soluble amino acids are selected from the group of proline, lysine, arginine, aspartate, glutamate and serine, including salts thereof and esters thereof. In particular, suitable salts include magnesium aspartate and lysine-glutamate salt. An example of a water soluble ester is N-acetyl cysteine.

In a particularly preferred embodiment, at least one water soluble amino acid is selected from the group of proline, lysine and arginine, including salts thereof and esters thereof. Specifically, good results have been realized with proline.

In Table 1, below, various amino acids are presented with their solubility at 20 degrees Celsius.

TABLE 1

Solubility of amino acids in water at 20 degrees Celsius

| Amino acid | Solubility (at 20° C.) (g/100 ml) |
|---|---|
| Cystine | 0.009 |
| Tyrosine | 0.038 |
| Aspartic acid | 0.42 |
| Glutamic acid | 0.72 |
| Tryptophan | 1.06 |
| Asparagine monohydrate | 2.36 |
| Leucine | 2.38 |
| Phenylalanine | 2.74 |
| Glutamine | 3.73 |
| Histidine | 3.84 |
| Isoleucine | 4.02 |
| Methionine | 4.8 |
| Valine | 5.75 |
| Threonine | 9 |
| Arginine | 14.8 |
| L-Alanine | 15.8 |
| Cysteine | 16 |
| L-histidine monohydrochloride monohydrate | 16.8 |
| N-acetyl cysteine | 17 |
| Glycine | 22.5 |
| Serine | 38 |
| L-glutamic acid Monohydrochloride | 38 |

TABLE 1-continued

Solubility of amino acids in water at 20 degrees Celsius

| Amino acid | Solubility (at 20° C.) (g/100 ml) |
|---|---|
| L-Arginine L-glutamate | 38 |
| L-Lysine monohydrochloride | 63 |
| Monosodium L-Aspartate monohydrate | 67 |
| Mono sodium L-glutamate monohydrate | 68 |
| Magnesium-L-aspartate | 69.4 |
| Arginine Monohydrochloride | 73 |
| L-Lysine-L-Glutamate | 81.4 |
| L-Lysine-L Glutamate dihydrate | 81.4 |
| Arginine Acetate | 85 |
| L-Ornithine L-aspartate | 88.3 |
| L-Arginin-L-aspartate | 93 |
| L-Lysine-L-Aspartate | 100 |
| Cysteine HCL-anhydrous | 102 |
| Cysteine HCl-Monohydrate | 110 |
| L-Lysine-Acetate | 140 |
| Proline | 155 |

As used herein, weight percent is the percentage of the weight relative to the total weight of the composition, unless stated otherwise. It is in short written as wt %.

As used herein, particles are solid structures (at 20° C.), composed of one or more solid materials, i.e. in case of amino acid particles, each of the particles are composed of one or more amino acids, and optionally one or more further ingredients, e.g. one or more vitamins and/or minerals. In particular, the particles may be microparticles. Typically, the (weight) average diameter of such particles ranges from approximately 10 nm to approximately 1000 µm. A preferred average diameter depends on the intended use. In general, the (weight) average diameter of the non-agglomerated or agglomerated particles preferably is at least 1 µm. In a particularly preferred embodiment, the non-agglomerated particles have a (weight) average particle size in the range of 1-100 µm. In particular, the particle diameter as used herein is the diameter as determinable by a Laser Diffraction Particle size analyzer. If the particles are too small or cannot be analysed by light scattering because of their optical properties, scanning electron microscopy (SEM) or transmission electron microscopy (TEM) can be used. Several types of particle structures can be prepared according to the invention. These include substantially homogenous structures, including microspheres and the like.

The particles of the invention are agglomerated particles (also referred to as agglomerates), i.e. a plurality of relatively small particles (which may be homogenous structures) that have clustered together to form a larger structure (an agglomerate). The water soluble amino acid facilitates the formation of the agglomerates, and also helps to hold the smaller particles together. The water soluble amino acid therefore functions as an agglomerant.

The agglomerated particles of the invention thus in particular comprise particles composed of at least one component selected from the group of lowly soluble amino acids and peptides (the 'relatively small particles', as referred to above), which are bound by one or more water soluble amino acids. The (particles comprising) the lowly soluble amino acid(s) may be at least partially embedded in or at least partially covered by one or more water soluble amino acids, e.g. on average for at least 50% of the surface. However, the invention also extents to agglomerated particles wherein only a minor part (on average less than 50%) of the surface of the (particles comprising) the lowly soluble amino acid(s) is covered. In principle, it is sufficient for the particles of the lowly soluble amino acid(s) to be bound together by the water soluble amino acid at a few spots (e.g. as provided by dried droplets of a solution comprising at least one water-soluble amino acid, for instance as obtainable in a method according to the invention, further described herein below) soluble amino acids.

Accordingly, the use of a water soluble amino acid, in particular an aqueous solution comprising a water soluble amino acid, as an agglomerant, is a further aspect of the invention.

The applicability of the amino acids as agglomeration agent has assessed in trials using Aeromatic agglomeration equipment. As an agglomeration agent, one or more amino acids selected from the group of proline, arginine, aspartate (in particular the magnesium salt), serine and lysine (in particular a salt of lysine and glutamate) are preferred. Of these, lysine, arginine, and proline are in particular preferred.

Besides amino acid particles, particles of other materials, e.g. vitamins, minerals, or other (micro)nutrients may be agglomerated using the water soluble amino acid(s) as an agglomerant. In particular, it is envisaged that the water soluble amino acid(s) may be used as an agglomerant for such materials having a solubility in water at 20° C. of less than 5 g/100 ml.

The inventors of the present invention further found that by agglomerating particles of the amino acid(s) having a solubility of less than 5 g/100 ml in the presence of an aqueous solution comprising one or more water-soluble amino acids and thereafter drying the formed agglomerates, agglomerated particles are obtained having improved wettability, compared to agglomerated particles obtained in a conventional agglomeration process, wherein water is sprayed on top of a powder mixture. It is contemplated that hereby dispersibility is improved.

Accordingly, the invention further relates to a method for preparing an agglomerated powder comprising at least one component selected from the group of peptides and amino acids, which may be present as a free amino acid or peptide, a salt thereof, or an ester thereof, the method comprising
  a) providing a powder comprising at least one component selected from the group of peptides and amino acids having a solubility of less than 5 g/100 ml water at 20° C. (which may be present as a free amino acid or peptide, as a salt thereof, or as an ester thereof), and optionally one or more amino acids having a solubility of at least 5 g/100 ml water at 20° C.
  b) preparing an aqueous solution comprising at least one amino acid (which may a free amino acid, as a salt thereof, or as an ester thereof), that has a solubility of at least 5 g/100 ml water at 20° C., the solution further optionally comprising at least one component selected from the group of vitamins and minerals;
  c) contacting the powder provided in step a) with the aqueous solution prepared in step b) and forming agglomerates; and
  d) drying the agglomerates, thereby providing the agglomerated powder.

An advantage of this approach is that no 'conventional' agglomeration agents such as maltodextrin, lecithine or the like, are necessary for preparing an amino acid powder mixture having a satisfactory dispersibility in water.

The method according to the invention has the additional advantage that the method is suitable to prepare an agglomerated product having a narrow agglomerated-particle size distribution and/or a wherein there a little or no differences in density between the different agglomerates. This is advantageous with respect to distributing particles more evenly in the loose powder, thereby preventing wrong dosing of the powder, due to possible differences in amino acid composition between individual particles. Further, a composition obtainable by a method of has a low tendency of dust formation.

The invention further relates to an agglomerated powder obtainable by a method according to the invention.

The powder of the lowly soluble peptide(s) and/or amino acid(s) for step a) of a method of the invention may be prepared in a manner known per se, or be a commercially available powder. If desired, a blend of particles with different amino acid compositions can be provided by mixing different powders (having different amino acid/peptides compositions), or a powder can be prepared from a blend of different amino acids and peptides (e.g. by spray drying a liquid blend). If desired, one or more further ingredients, e.g. one or more vitamins, one or more minerals and/or other (micro)nutrients can be admixed.

The contacting of the powder of step a) with the aqueous solution of step b) typically takes place in an agglomeration unit, such as a fluidized bed (fluid bed). The solution is in general sprayed or nebulized into the fluidized bed wherein it will be intimately contacted with the fluidized powder. The water soluble amino acid(s) are thought to facilitate the sticking together of the fluidized particles, whereby agglomerated particles according to the invention are formed.

Suitable process conditions for agglomeration can be based on common general knowledge, supplier guidelines for the agglomeration unit that is used, the information disclosed herein and optionally a limited amount of routine testing.

The concentration of the water soluble amino acid(s) and its (their) solubility in water determines to a large extent the function of the amino acids as an agglomeration agent. A relatively high concentration is in particular preferred for reasons such as agglomeration efficiency, reduced process time (reduced agglomeration time and/or drying time) and energy consumption for drying (compared to use of a less concentrated solution wherein the same weight of amino acid(s) is applied to the particles). The reduced process time is not only preferred for practical reasons (higher production capacity) but also is beneficial with respect to degradation of (amino acid(s) in) and avoiding undesired side-reation, in particular if agglomeration and/or drying takes place while heating.

Usually, the concentration of the water soluble amino acid(s) is between 5 g/100 ml and the saturation concentration of the water soluble amino acid, or in case more than one water soluble amino acid is used, the sum of their saturation concentrations. Preferably, the total concentration of the water soluble amino acid(s) in the aqueous solution is between 5 and 200 g/100 ml, more preferably between 10 and 155 g/100 ml. In a specific embodiment the total concentration of the water soluble amino acid(s) in the aqueous solution is at least 20 g/100 ml.

As a rule of thumb, the contacting and/or the drying preferably takes place at a temperature in the range of from ambient temperature to about 60° C., in particular at a temperature in the range of 20-40° C.

The ratio powder to aqueous solution can be chosen within wide limits. The skilled person will be able to determine a sufficient amount of water relative to the powder to cause the powder particles to stick together, aided by the water soluble amino acid, based on common general knowledge, the information disclosed herein and optionally a limited amount of routine testing. Usually sufficient solution will be added to increase the water activity of the powder that is being agglomerated to a value above 0.3, whilst the amount is chosen low enough such that substantial dissolution of the particles is avoided and that fluidization of the particles is maintained.

Thus, during agglomeration, in general a relatively wet agglomerate is formed, compared to the final product.

The drying can be carried out in a matter known per se and is usually proceeded to provide an agglomerate powder having a water activity of 0.3 or less, in particular of 0.1-0.3. In a particularly preferred embodiment the water activity of the dried powder is 0.2.

In practice, the drying can commence while the agglomeration proceeds.

If desired, the dried agglomerated powder can be subjected to a size fractionation step, for instance sieving or by using a cyclone. If desired, particles that have not agglomerated, or agglomerates that are undesirably small can be returned to the agglomeration unit. Further, undesirably large agglomerates can be removed, and returned to the agglomeration unit if desired. In particular, in case the undesirably large agglomerates are still relatively wet (water activity >0.3), they may be returned to the agglomeration unit (or drying unit, if separate from the agglomeration unit) without a size reduction treatment. Alternatively, they are subjected to a size reduction treatment before be returned to the agglomeration unit or discarded from the process.

As indicated above, the total concentration of the component or components selected from the group of amino acids and peptides, including esters thereof and salts thereof, having a solubility in water at 20 degrees Celsius of less than 5 g/100 ml in the agglomerated amino acid particles (such as an agglomerated powder) is between 1 and 95 wt % of the weight of the particles. Said concentration preferably is at least 2 wt %. Said concentration preferably is 90 wt % or less.

The total concentration of amino acids having a solubility in water at 20 degrees Celsius of at least 5 g/100 ml, in particular of at least 10 g/100 ml, more in particular of at least 15 g/100 ml in the agglomerated particles, is in the range of 2-99 wt %. In particular, said concentration may be at least 4 wt %, more in particular at least 5 wt %, e.g. at least 10 wt %.

The total concentration of amino acids and peptides in the agglomerated particles is in general 50 wt % or more, in particular at least 75 wt %, more in particular at least 85 wt %. The total concentration may be 100 wt % or less, in particular 95 wt % or less. In a specifically preferred embodiment the total concentration of amino acids or peptides is between 90 and 100% since with the method according to the present invention it is possible to make agglomerates without other agglomerating agents.

The balance, if any, may in particular be formed from the group consisting of excipients and further nutrients. The nutrients, in particular micro-nutrients, e.g. vitamins, minerals and the like, may also have a low solubility/dispersibility in water. As an excipient, e.g. a maltodextrin may be used, or another carbohydrate known to be suitable to that purpose. Further, fat and/or one or more other macronutrients may be included.

If present, the one or more further components, such as excipients, fat, vitamins and/or minerals, are preferably blended (as separate particles) with the amino acid (particles) having a solubility of less than 5 g/100 ml water, prior to contacting with the aqueous solution.

The agglomerated amino acid particles may be used as such, e.g. as a dietary supplement, usually after dispersing in water or an aqueous liquid.

Alternatively, the agglomerated amino acid particles may be used for preparing a nutritional, nutraceutical, or pharmaceutical product comprising one or more further ingredients, as desired.

Accordingly, the present invention further relates to a product comprising agglomerated amino acid particles and at least one food-grade or pharmaceutically acceptable component.

For instance, a composition, in particular a blend, may be provided comprising the agglomerated amino acid particles and one or more components selected from the group of lipids (fats), carbohydrates (digestible or indigestible), proteins, (additional) minerals, (additional) vitamins, (additional) pharmaceutically acceptable excipients and the like, as are known in the art.

Preferably, the nutritional, nutraceutical, or pharmaceutical product is a powder.

Preferably a nutritional product according to the invention comprises at least one compound selected from the group of fats, digestible carbohydrates, indigestible carbohydrates, vitamins and minerals.

In addition, if one or more carbohydrates and/or one or more fats are present, the claimed method of preparing the amino acid mixtures has an unexpected positive effect on the taste and stability of the composition. Without being bound by theory, it is hypothesized that this effect is due to the absence of maillard reactions (or at least a reduced extent of maillard reactions) during the agglomeration of the amino acids. In particular for that reason, Therefore, also if fat and carbohydrates are present, the present amino acid preparation is a preferred way of preparing nutritional formula comprising amino acids as a source for protein.

A nutritional product according to the invention preferably contains between 5 and 50 wt % amino acids (in general at least substantially provided for by the agglomerated particles of the invention), 5-80 wt % digestible carbohydrates, and 2-25 wt % fat, based on dry weight. The balance, if any, is usually at least substantially formed by one or more of the further components, as mentioned above.

Preferred examples of nutritional products according to the invention include infant formulations, clinical foods, and in particular various products from the metabolic range, such as products intended for subjects that have an amino acid related metabolic disorder, e.g. phenyl keton urea (PKU).

For instance, specific commercial formulations that could benefit from the present invention are compositions, as known under the brand name Neocate, Elecare, Easyphen.

For instance, products that are intended to reduce the entry of phenylalanine in the brain of Phenyl keton urea (PKU) patients by competitive inhibition using long neutral amino acids (LNAA) are thought to benefit from the present invention, since several LNAA have a low solubility and dispersibility in water, and have a low palatability.

The term LNAA is used herein in particular for the group of amino acids formed by leucine, isoleucine, valine, phenylalanine, and tryptophan.

Therefore, a preferred embodiment of the present invention is a dietary supplement comprising an agglomerated amino acid admixture, comprising—in wt %: Histidine 12-16, isoleucine 5.5-8.0, leucine 7-15, methionine 12-15, threonine 7-16, tryptophane 9-16, tyrosine 12-16, valine 7-9. The admixture is agglomerated with one or more water soluble amino acids. Preferably the at least one water soluble amino acid is selected from the group of lysine and arginine. If present, the lysine content preferably is 5-8 wt %, based on the total weight of the supplement. The arginine content preferably is 0-4 wt %, based on the total weight of amino acids in the supplement.

Preferably a micronutrient fraction is present in the admixture which provides 3.65-4.0 µg of selenium and 0.20-0.22 µg of vitamin B12 for each gram of the LNAA fraction.

If the product is intended for PKU patients, it is free of phenyl alanine.

Next, the invention is illustrated by a number of Examples.

EXAMPLES

Example 1

Determination of Wettability (GEA Niro Method No. A 5 b)

Apparatus
  Balance (sensitivity 0.01 g).
  Weighing dish.
  600 ml beaker, internal diameter 90 mm±2 mm and height 120 mm±3 mm, glass plate and glass or stainless steel tube (see FIG. 1).
  250 ml beaker.
  Small brush.
  Stop watch.
  Thermometer, 0-100° C. (calibrated to within ±0.5° C.).
Materials
  Deionised water.
Procedure
  6.1 Weigh a 10 g±0.05 g well mixed instant dried milk into a weighing dish.
  6.2 Measure 250 ml±1 ml of deionised water adjusted to 25° C.±0.5° C. into a dry 600 ml glass beaker ensuring that the inside of the beaker above the final water level remains dry.
  6.3 Place the steel plate on top of the beaker, with one edge of the plate close to the rim of the beaker. Place the glass tube on top of the plate as shown in FIG. 1.
  6.4 Transfer the test portion from the weighing dish to the glass tube, and spread the sample evenly over the glass plate.
  6.5 Start the stop watch. After 10 seconds, withdraw the glass plate with one hand (holding the steel tube with the other hand) allowing the powder sample to fall progressively, over a period of 2.5 seconds, onto the surface of the water.
  6.6 Record the time in seconds from the beginning of withdrawal of the glass plate until all the particles have become wetted.
  6.7 Measurements are to be carried out in duplicate.
7 Result
  The wetting time (wettability)=T−10
  where:
    T=time recorded (in 6.6) in seconds.
    10=time elapsed before withdrawal of the glass plate.

Example 2

A proline solution (25% w/w) was sprayed onto a powder mixture, consisting of particles of individual amino acids (86.8 g/100 g), mineral particles (11 g/100 g), vitamin particles (1.08 g/100 g) and maltodextrin particles (excipient) (1.12 g/100 g). The fluidization was done at ambient conditions (approx. 20° C.), using Glatt agglomeration equipment. During the process, 42 g of the 25% proline solution was sprayed onto approximately 200 g of the powder mixture. After spraying the proline solution the mixture was dried by fluidization at 55° C. for 5 minutes, decreasing the water activity (Aw) back to its original value (0.2).

The wettability (time to wet and disperse the particles evenly over the solution) improved from more than 120 sec. (max. time of analysis) for the comparative product to 1 sec. Fine and light particles were incorporated in the granules and did not give dust upon scooping anymore.

Upon composing the powder mixture the proline was not included. The required amount of proline in the end composition was fully added through spraying a solution of proline onto the powder mixture.

Variations of the above experiment have been performed in pilot scale trials with the following results:
  The results are also valid for powder mixtures with other amino acid compositions.
  The applied drying temperature can vary between 20 and 60° C., the higher the temperature, the shorter the required drying time.
  The same results (improved wettability, reduced dusting) can be achieved by a lower amount of sprayed proline (other examples: 2.5 wt %-4.3 wt % proline, based on total amino acid content in the dry product))
Similar results for the cases of
  Spraying a 40 wt % proline solution
  Spraying 50 wt % proline solution
  Spraying a 10 wt % arginine solution

Example 3

Production Scale Example

A powder mixture was provided as shown in Table 2:

TABLE 2

|  | wt % |
|---|---|
| L-ALANINE | 3.3 |
| L-ARGININ-L-ASPARTATE | 4.7 |
| L-ASPARTIC ACID | 2.0 |
| L-CYSTINE | 1.9 |
| L-GLUTAMIC ACID | 5.5 |
| L-GLUTAMIN | 5.5 |
| GLYCINE | 1.9 |
| L-HISTIDINE BASE | 1.9 |
| L-ISO-LEUCINE | 4.7 |
| L-LEUCINE | 7.8 |
| L-LYSINE-L-GLUTAMATE DIHYDRATE | 12.4 |
| L-METHIONINE | 1.9 |
| L PROLINE | 7.4 |
| L-SERINE | 4.1 |
| L-THREONINE | 3.7 |
| L-TRYPTOPHAN | 1.4 |
| L-TYROSINE | 5.6 |
| L-VALINE- | 5.5 |
| MAGNESIUM L-ASPARTATE | 4.7 |
| FAT MIXTURE | 2.8 |
| VANILLIN | 0.05 |
| L-CARNITINE | 0.140 |
| MINERALS | 10.000 |
| VITAMINS | 1 |
|  | 100.00 |

The powder mixture, total 55.5 kg, was heated to 40° C. for 10 minutes. A proline solution (50% w/w, total 9.9 kg) was prepared using hot water. The proline solution was fed through a spray lance of the agglomeration equipment using a variable speed peristaltic pump. It took 25 minutes to transfer all of the solution onto the powder. During the agglomeration the fluidization air was kept at 40° C. After agglomeration (during 25 minutes) the product was dried in the agglomeration tower for another 10 minutes (temperature kept at 40° C.). After drying the agglomerated mixture was taken out and samples for analysis were taken. The product was then sieved in order to eliminate the oversize particles from the mixture. The product was further assessed on wettability and water activity. The wettability was reduced from more than 120 seconds (non-agglomerated sample) to less than 10 seconds.

TABLE 3 preferred nutritional amino acid compositions (wt. % for amino acids; ug/g LNAA for B12 and Se).

| | pref. range | A | B | C | D | E | F | G |
|---|---|---|---|---|---|---|---|---|
| Histidine | 3.5-16 | 15.4 | 12.5 | 4 | 4.3 | 3.8 | 5.1 | 5 |
| Isoleucine | 0-8 | 7.7 | 5.9 | 6.1 | 6 | 6.1 | 0 | 0 |
| Leucine | 0-8 | 7.7 | 15 | 10.5 | 10.3 | 10.3 | 0 | 0 |
| Methionine | 1.5-16 | 15.4 | 12.5 | 1.7 | 1.7 | 1.64 | 2.2 | 2.1 |
| Phenyl-alanine | 0-6.5 | 0 | 0 | 0 | 0 | 0 | 6 | 6.1 |
| Tryptophan | 2-16 | 15.4 | 9.2 | 2.1 | 2 | 2 | 2.7 | 2.7 |
| Tyrosine | 2-16 | 15.4 | 12.5 | 9.3 | 9 | 9 | 6 | 6.1 |
| Valine | 0-9 | 7.7 | 8.5 | 6.7 | 6.3 | 6.6 | 0 | 0 |
| Threonine | 4.5-15 | 7.7 | 15 | 5.2 | 5 | 4.9 | 6.7 | 6.7 |
| Lysine | 5-10 | 7.7 | 5.9 | 7.1 | 7.6 | 7.8 | 9.3 | 9.3 |
| Arginine | 0-10 | 0 | 3 | 6.9 | 7.6 | 6.7 | 9 | 9.1 |
| B12 | 0-0.4 | 0.19 | 0.11 | 0.35 | 0.06 | 0.03 | 0.02 | 0.02 |
| Selenium (Se) | 0-4 | 4 | 2.1 | 0.46 | 0.59 | 0.54 | 0.28 | 0.3 |

In the above compositions the amino acids valine, threonine, lysine or arginine have a solubility higher than 5 g/100 ml and can thus be used as agglomeration agent according to the invention.

The invention claimed is:

1. Method for the preparation of an agglomerated powder comprising at least one component selected from the group consisting of peptides and amino acids, which may be present as a free amino acid or peptide, a salt thereof, or an ester thereof, comprising
   a) providing powder particles comprising at least one component selected from the group consisting of peptides and amino acids having a solubility of less than 5 g/100 ml water at 20° C. which may be present as a free amino acid or peptide, a salt thereof, or an ester thereof, and optionally one or more amino acids having a solubility of at least 5 g/100 ml water at 20° C.;
   b) preparing an aqueous solution comprising at least one amino acid which may a free amino acid, a salt thereof, or an ester thereof, that has a solubility of at least 5 g/100 ml water at 20° C., the solution further optionally comprising at least one component selected from the group consisting of vitamins and minerals;
   c) contacting the powder particles provided in step a) with the aqueous solution prepared in step b) and agglomerating said particles comprising at least one component selected from the group consisting of peptides and amino acids having a solubility of less than 5 g/100 ml water at 20° C. thereby forming agglomerates comprising said particles comprising at least one component selected from the group consisting of peptides and amino acids having a solubility of less than 5 g/100 ml water at 20° C.; and
   d) drying the agglomerates, thereby providing the agglomerated powder.

2. Method according to claim 1, wherein in step a) at least one amino acid is selected from the group consisting of glutamine, leucine, isoleucine, valine, threonine, tyrosine, phenylalanine, asparagine, histidine, methionine, cystine and tryptophane.

3. Method according to claim 1, wherein at least one amino acids in step b) is selected from the group consisting of proline, lysine and arginine.

4. Method according to claim 1, wherein the powder comprises particles comprising the at least one component selected from the group consisting of peptides and amino acids having a solubility of less than 5 g/100 ml water at 20° C. and wherein during the forming of the agglomerates the particles are bound together by the water soluble amino acid.

5. Method according to claim 1, wherein the contacting of the powder and the aqueous solution takes place in a fluidized bed.

6. Method according to claim 5, wherein the aqueous solution is sprayed or nebulized into the fluidized bed wherein the powder is fluidized and the aqueous solution is intimately mixed with the fluidized powder.

7. Method according to claim 1, wherein agglomerated amino acid particles are formed comprising between 1 and 95 wt % of at least one component selected from the group of amino acids and peptides, including esters thereof and salts thereof, having a solubility in water at 20° Celsius of less than 5 g/100 ml, wherein said at least one component is agglomerated with at least one water soluble amino acid, which may be a free amino acid, an ester thereof or a salt thereof, having a solubility in water at 20° Celsius of at least 5 g/100 ml, wherein the concentration of said water soluble amino acid is at least 5 wt. %, wherein the composition comprises an amino acid admixture of amino acids having solubility in water at 20° Celsius of less than 5 g/100 ml, the admixture comprising 12-16 wt % histidine, 5.5-8.0 wt % isoleucine, 7-15 wt % leucine, 12-15 wt % methionine, 7-16 wt % threonine, 9-16 wt % tryptophan, 12-16 wt % tyrosine, and 7-9 wt % valine, all weight percentages being based on the total weight of the agglomerated particles and wherein the agglomerated amino acid particles are a powder having a time to wet of less than 60 seconds, as determined by GEA Niro Method No. A 5 b or as determined by IDF standard 87 (1979).

8. Method according to claim 7, wherein agglomerated amino acid particles are formed comprising 5-8 wt % lysine and 0-4 wt % arginine, all weight percentages being based on the total weight of the agglomerated particles.

9. Method according to claim 7, wherein the agglomerated particles are formed comprising at least one large neutral amino acid (LNAA) and further at least one micronutrient is present in the composition which provides 3.65-4.0 μg of selenium and 0.20-0.22 μg of vitamin B12 for each gram of the LNAA.

10. Method according to claim 1, wherein the powder further comprises particles of at least one component selected from the group consisting of vitamins and minerals.

11. Method according to claim 5, wherein the amount of aqueous solution in step c) is sufficient to increase the water activity of the powder that is being agglomerated to a value above 0.3 while the amount is chosen such that substantial dissolution of the particles is avoided and that fluidization of the particles is maintained.

* * * * *